(12) United States Patent
Tompkins et al.

(10) Patent No.: US 11,523,830 B2
(45) Date of Patent: *Dec. 13, 2022

(54) EMBOLIC COIL IMPLANT SYSTEM AND IMPLANTATION METHOD

(71) Applicant: Penumbra, Inc., Alameda, CA (US)

(72) Inventors: Ben Tompkins, Danville, CA (US); Arani Bose, New York, NY (US); Delilah Hui, American Canyon, CA (US); David Barry, Livermore, CA (US); Stephen Pons, Alameda, CA (US); Aleksander Leynov, Walnut Creek, CA (US)

(73) Assignee: Penumbra, Inc., Alameda, CA (US)

( * ) Notice: Subject to any disclaimer, the term of this patent is extended or adjusted under 35 U.S.C. 154(b) by 606 days.

This patent is subject to a terminal disclaimer.

(21) Appl. No.: 16/532,742

(22) Filed: Aug. 6, 2019

(65) Prior Publication Data

US 2020/0214717 A1     Jul. 9, 2020

Related U.S. Application Data

(60) Continuation of application No. 15/691,579, filed on Aug. 30, 2017, now Pat. No. 10,405,868, which is a
(Continued)

(51) Int. Cl.
*A61B 17/12* (2006.01)
*A61B 17/00* (2006.01)

(52) U.S. Cl.
CPC .... *A61B 17/12154* (2013.01); *A61B 17/1214* (2013.01); *A61B 17/12022* (2013.01);
(Continued)

(58) Field of Classification Search
CPC ........ A61B 17/12022; A61B 17/12113; A61B 17/1214; A61B 17/12145; A61B 17/12154; A61B 2017/12054
See application file for complete search history.

(56) References Cited

U.S. PATENT DOCUMENTS 5,261,916 A    11/1993   Engelson
5,304,195 A     4/1994   Twyford, Jr. et al.
(Continued)

FOREIGN PATENT DOCUMENTS

CN    1925796 A    3/2007
EP    0832607 A1   4/1998
(Continued)

OTHER PUBLICATIONS

Notice of allowance dated May 1, 2019 for U.S. Appl. No. 15/691,579.
(Continued)

*Primary Examiner* — Ashley L Fishback
(74) *Attorney, Agent, or Firm* — Haley Guiliano LLP

(57) ABSTRACT

Embolic coil implant systems and methods whereby coils are mechanically detachable are disclosed. The coils include a retention element that may be releasably retained within the distal end of an implant tool. The implant tool may include a fulcrum configured to engage a first filament and prevent the release of the coil when the first filament is engaged. Alternatively, an urging means and aperture may be disposed within the sidewall of the implant tool, and a first filament may, in conjunction with the aperture and sidewall, releasably retain the coil until the first filament is withdrawn. The implant tool may also include an alignment member for aligning the first filament.

15 Claims, 11 Drawing Sheets

Related U.S. Application Data continuation of application No. 15/383,241, filed on Dec. 19, 2016, now Pat. No. 9,775,621, which is a continuation of application No. 14/460,234, filed on Aug. 14, 2014, now Pat. No. 9,554,805, which is a continuation of application No. 13/680,596, filed on Nov. 19, 2012, now Pat. No. 9,186,151, which is a division of application No. 12/498,752, filed on Jul. 7, 2009, now Pat. No. 8,333,796.

(60) Provisional application No. 61/083,111, filed on Jul. 23, 2008, provisional application No. 61/080,742, filed on Jul. 15, 2008.

(52) U.S. Cl.
CPC .. *A61B 17/12113* (2013.01); *A61B 17/12145* (2013.01); *A61B 17/12181* (2013.01); *A61B 2017/00871* (2013.01); *A61B 2017/1209* (2013.01); *A61B 2017/12054* (2013.01)

(56) References Cited

U.S. PATENT DOCUMENTS

| | | | |
|---|---|---|---|
| 5,350,397 | A | 9/1994 | Palermo et al. |
| 5,800,454 | A | 9/1998 | Jacobsen et al. |
| 5,853,418 | A | 12/1998 | Ken et al. |
| 5,891,058 | A | 4/1999 | Taki et al. |
| 5,891,130 | A | 4/1999 | Palermo et al. |
| 5,895,391 | A | 4/1999 | Farnholtz |
| 6,551,340 | B1 | 4/2003 | Konya et al. |
| 8,333,796 | B2 | 12/2012 | Tompkins et al. |
| 9,186,151 | B2 | 11/2015 | Tompkins et al. |
| 9,554,805 | B2 | 1/2017 | Tompkins et al. |
| 9,775,621 | B2 | 10/2017 | Tompkins et al. |
| 10,405,868 | B2 | 9/2019 | Tompkins et al. |
| 2005/0192621 | A1 | 9/2005 | Wallace et al. |
| 2006/0276832 | A1 | 12/2006 | Balgobin et al. |
| 2007/0167981 | A1 | 7/2007 | Opolski et al. |
| 2007/0293928 | A1 | 12/2007 | Tomlin |
| 2008/0097462 | A1 | 4/2008 | Mitelberg et al. |
| 2010/0030200 | A1 | 2/2010 | Strauss et al. |

FOREIGN PATENT DOCUMENTS

| | | |
|---|---|---|
| EP | 1728477 A1 | 12/2006 |
| EP | 1797833 A1 | 6/2007 |
| EP | 1813213 A2 | 8/2007 |
| WO | WO-9311719 A1 | 6/1993 |
| WO | WO-9311825 A1 | 6/1993 |
| WO | WO-9406502 A2 | 3/1994 |
| WO | WO-9902094 A1 | 1/1999 |
| WO | WO-2007070797 A2 | 6/2007 |
| WO | WO-2007121405 A2 | 10/2007 |

OTHER PUBLICATIONS

Office action dated Mar. 28, 2019 for U.S. Appl. No. 15/691,579.
"Office action dated May 15, 2015 for U.S. Appl. No. 14/460,234.".
"Office action dated Oct. 6, 2015 for U.S. Appl. No. 14/460,234.".
International search report and written opinion dated Dec. 22, 2009 for PCT/US2009/050319.
Notice of allowance dated Jul. 22, 2014 for U.S. Appl. No. 13/680,596.
Notice of Allowance dated Aug. 2, 2017 for U.S. Appl. No. 15/383,241.
Notice of allowance dated Sep. 30, 2016 for U.S. Appl. No. 14/460,234.
Notice of allowance dated Oct. 1, 2012 for U.S. Appl. No. 12/498,752.
Office Action dated Feb. 7, 2017 for U.S. Appl. No. 15/383,241.
Office action dated Feb. 14, 2014 for U.S. Appl. No. 13/680,596.
Office action dated Mar. 30, 2011 for U.S. Appl. No. 12/498,752.
Office Action dated Jun. 17, 2016 for U.S. Appl. No. 14/460,234.
Office action dated Sep. 14, 2011 for U.S. Appl. No. 12/498,752.
Office action dated Oct. 7, 2014 for U.S. Appl. No. 14/460,234.

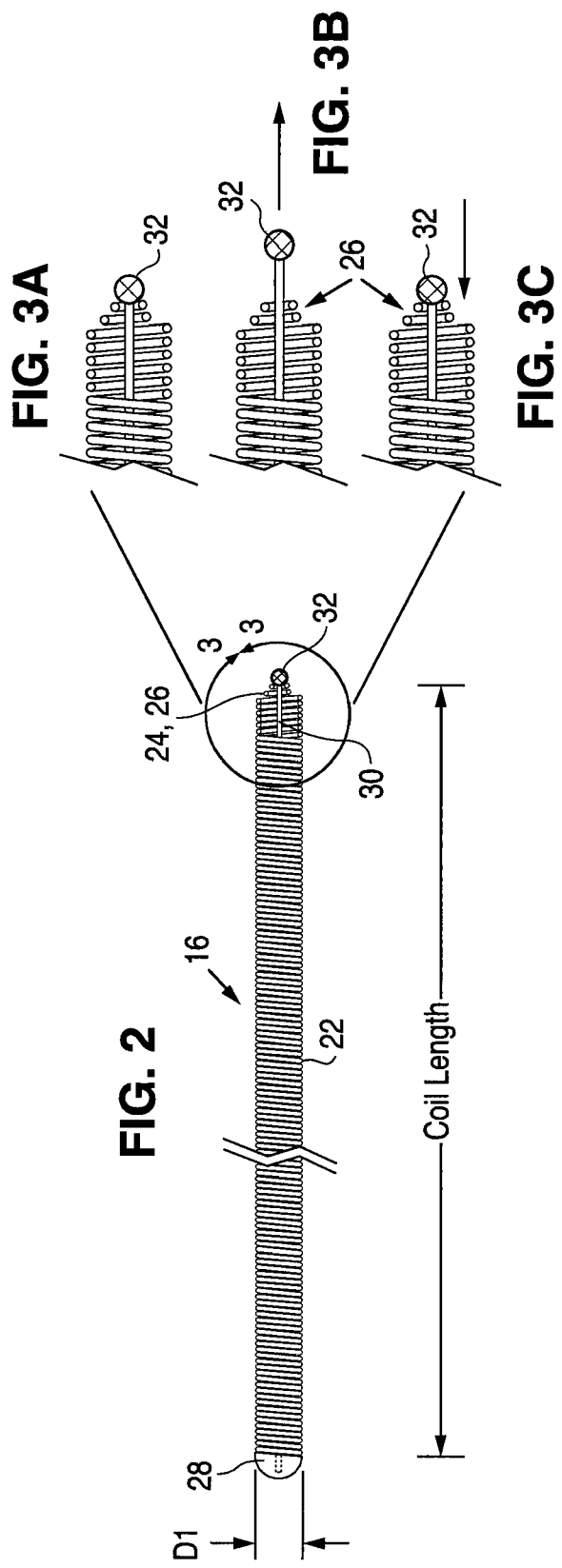

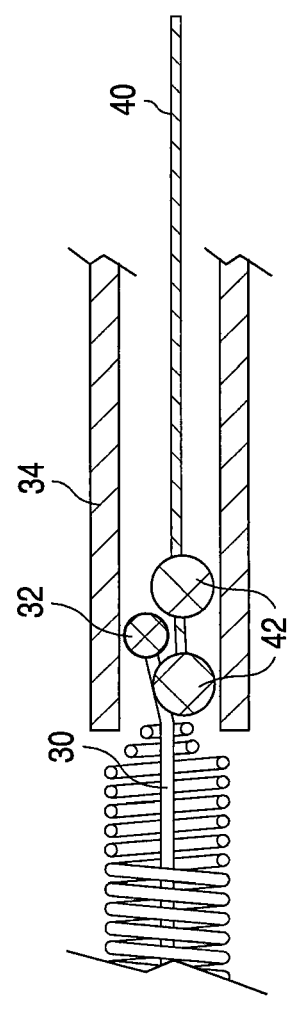
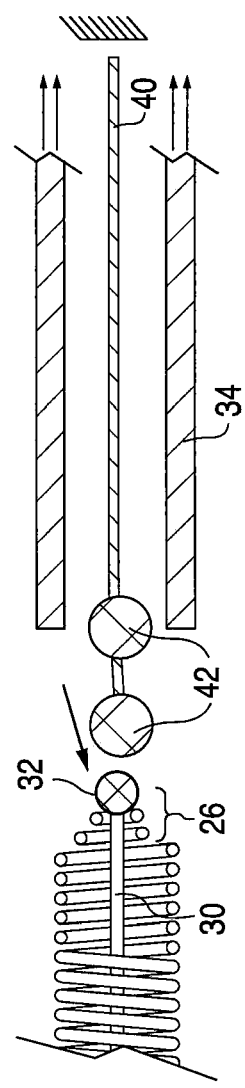

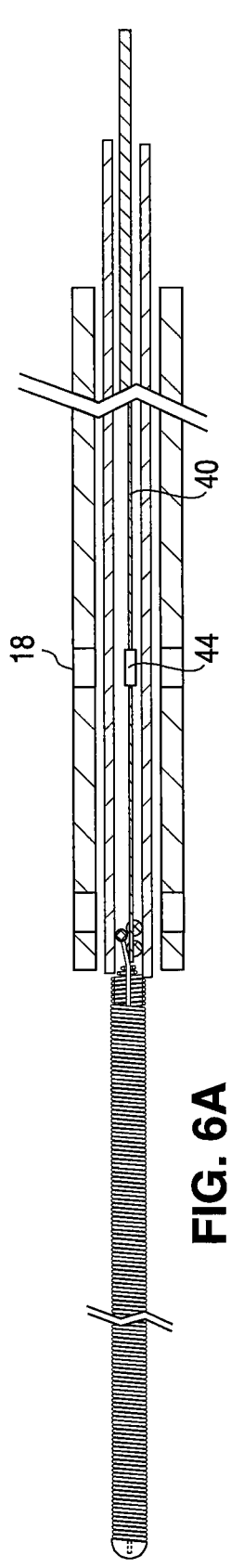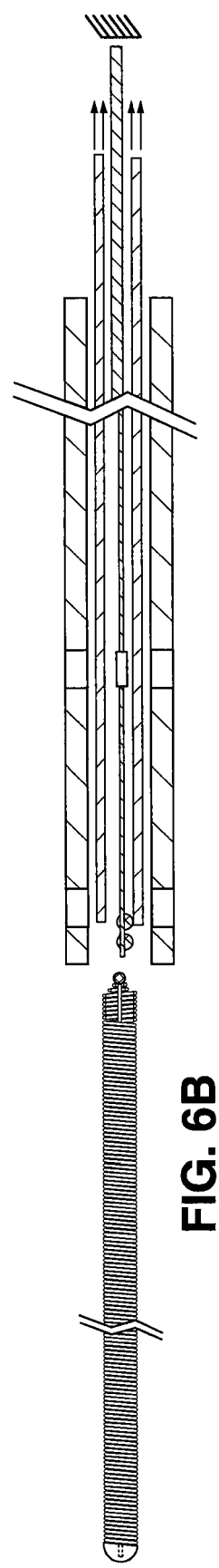

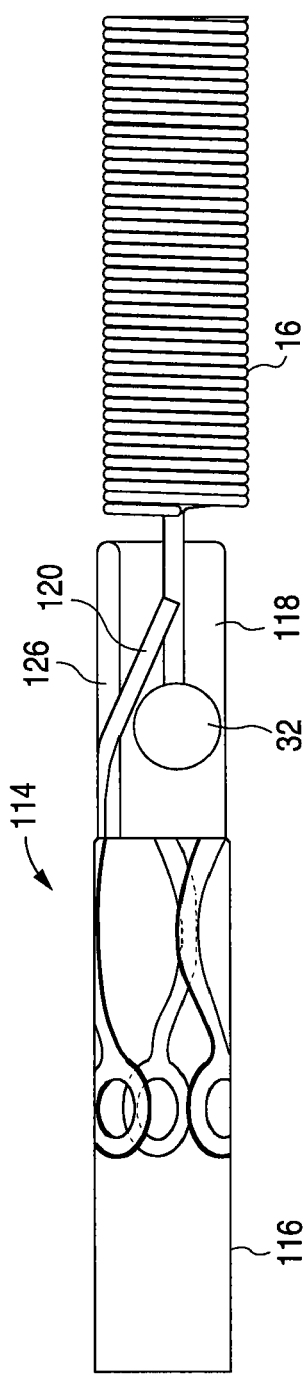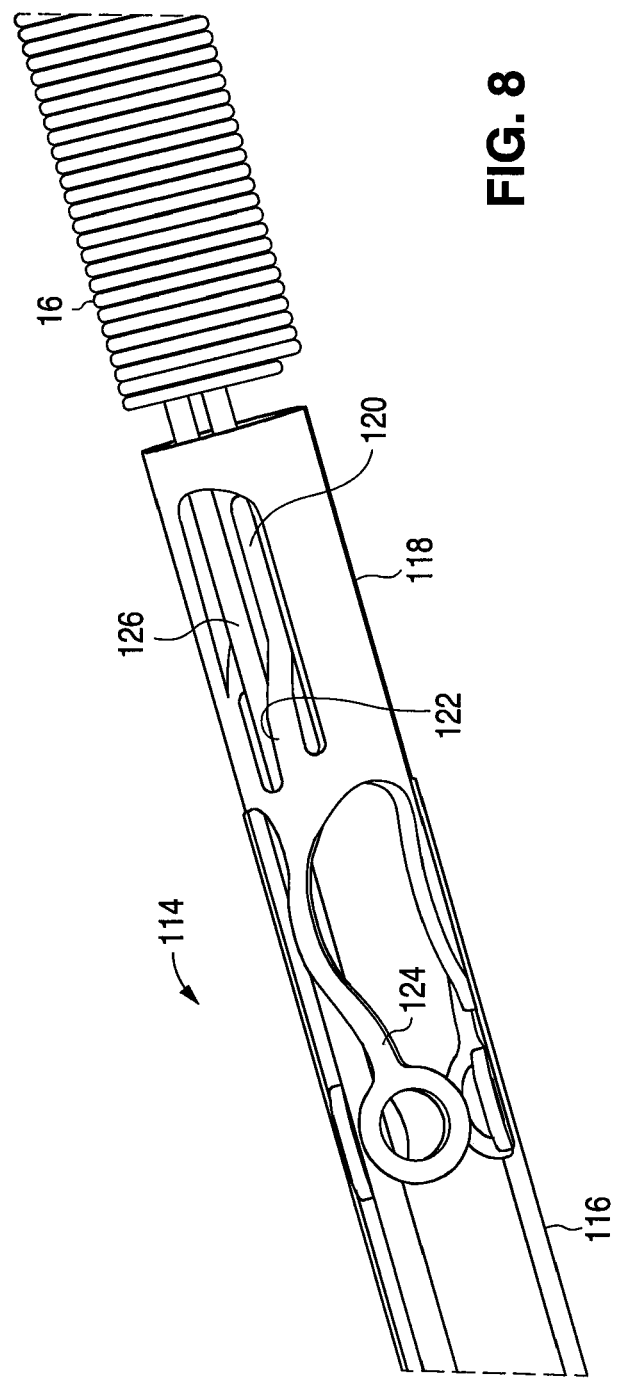

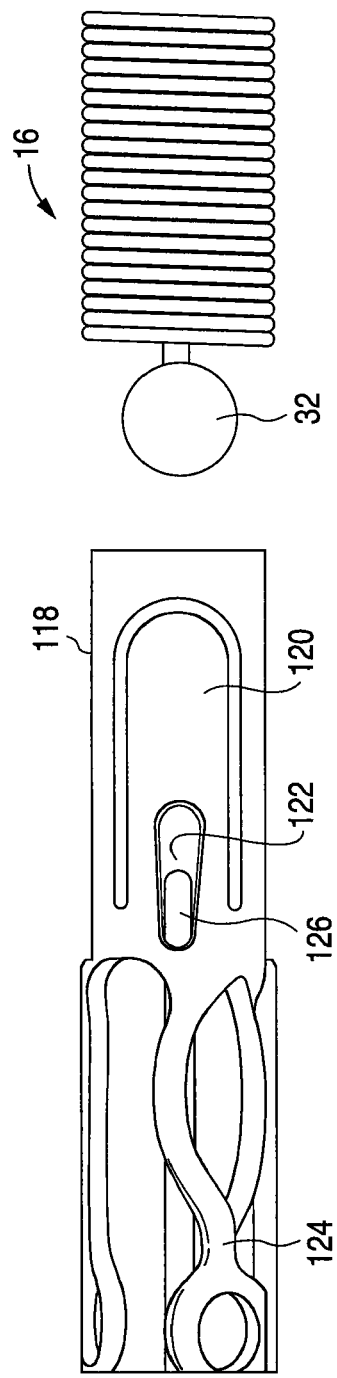
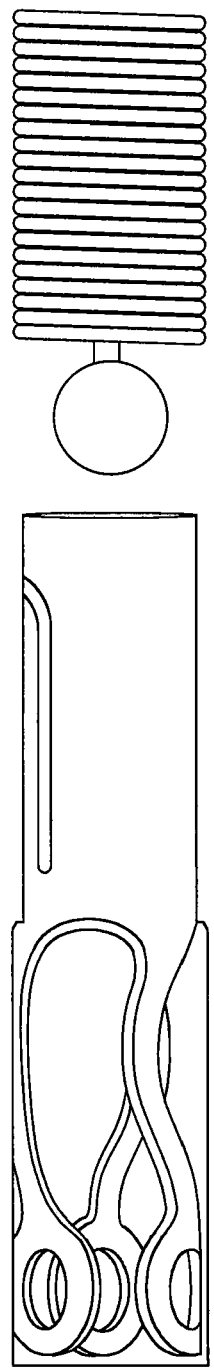
FIG. 9
FIG. 10

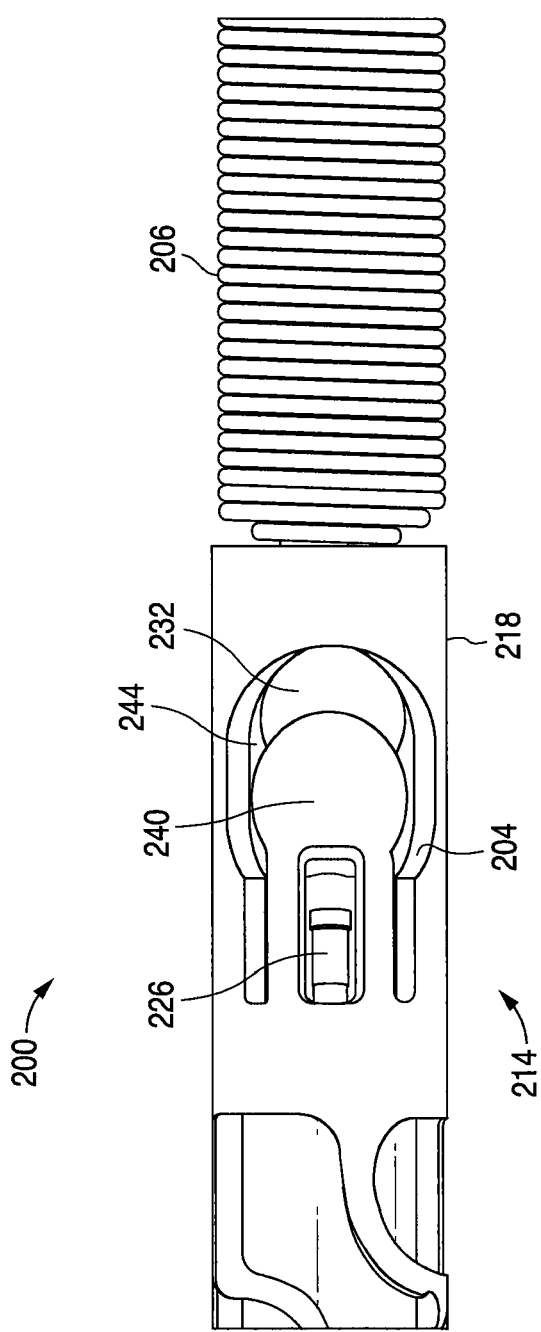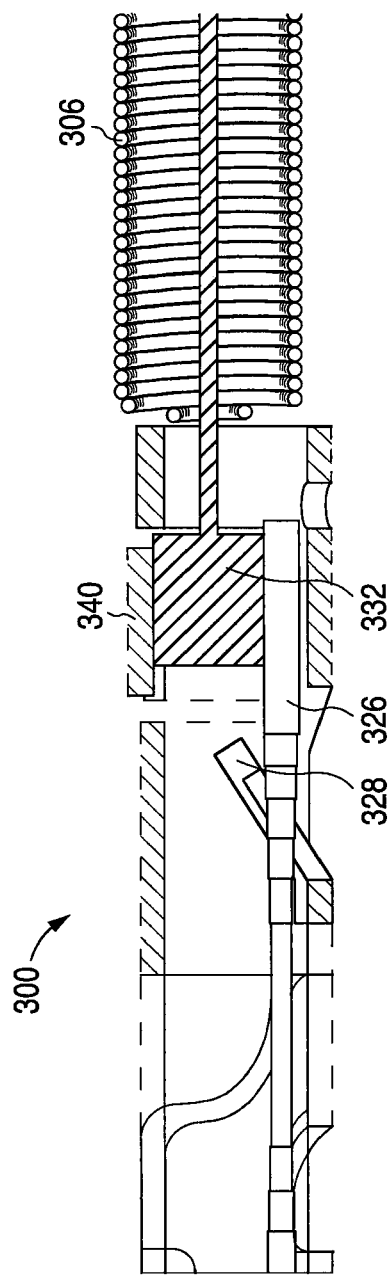

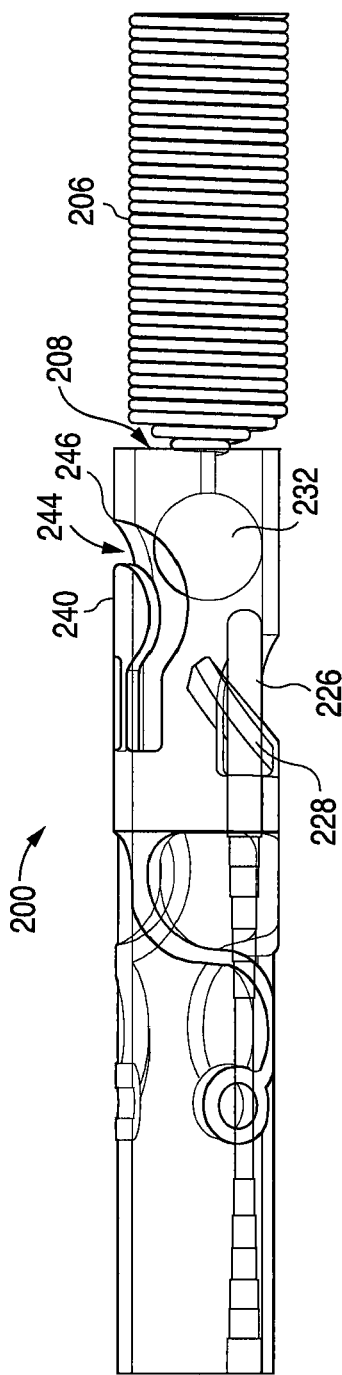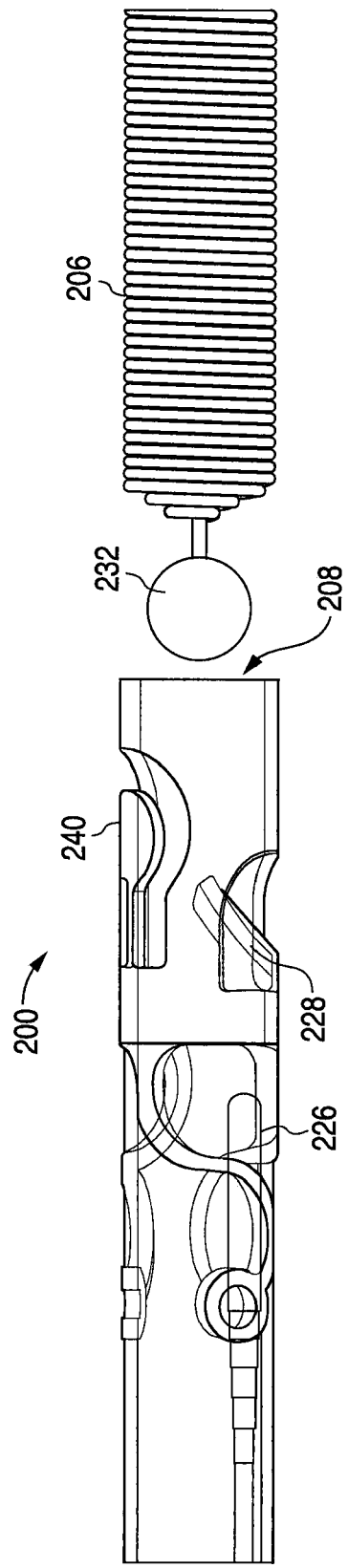

EMBOLIC COIL IMPLANT SYSTEM AND IMPLANTATION METHOD

CROSS-REFERENCES TO RELATED APPLICATIONS

This application is a continuation of U.S. patent application Ser. No. 15/691,579, filed Aug. 30, 2017, now U.S. Pat. No. 10,405,868, which is a continuation of U.S. patent application Ser. No. 15/383,241, filed Dec. 19, 2016, now U.S. Pat. No. 9,775,621, which is a continuation of U.S. patent application Ser. No. 14/460,234, filed Aug. 14, 2014, now U.S. Pat. No. 9,554,805, which is a continuation of U.S. patent application Ser. No. 13/680,596, filed Nov. 19, 2012, now U.S. Pat. No. 9,186,151, which is a divisional of U.S. patent application Ser. No. 12/498,752, filed Jul. 7, 2009, now U.S. Pat. No. 8,333,796, which claims priority to Provisional Application No. 61/080,742, filed Jul. 15, 2008, and Provisional Application No. 61/083,111, filed Jul. 23, 2008, the disclosures of which are incorporated herein by reference.

BACKGROUND OF THE INVENTION

1. Field of the Invention

The present invention relates generally to the fields of systems and methods for implanting an intravascular implant device, and more specifically to systems and methods for implanting embolic coils.

BRIEF SUMMARY OF THE INVENTION

Coil embolization is a commonly practiced technique for treatment of brain aneurysm, arterio-venous malformation, and other conditions for which vessel occlusion is a desired treatment option, such as, for example, in the occlusion of a tumor "feeder" vessel. A typical occlusion coil is a wire coil having an elongate primary shape with windings coiled around a longitudinal axis. In the aneurysm coil embolization procedure, a catheter is introduced into the femoral artery and navigated through the vascular system under fluoroscopic visualization. The coil in the primary shape is positioned within the catheter. The catheter distal end is positioned at the site of an aneurysm within the brain. The coil is passed from the catheter into the aneurysm. Once released from the catheter, the coil assumes a secondary shape selected to optimize filling of the aneurysm cavity. Multiple coils may be introduced into a single aneurysm cavity for optimal filling of the cavity. The deployed coils serve to block blood flow into the aneurysm and reinforce the aneurysm against rupture.

One form of delivery system used to deliver an embolic coil through a catheter to an implant site includes a wire and a coil attached to the wire. The coil (with the attached wire) is advanced through a catheter as discussed above. To release the coil into an aneurysm, current is passed through the wire, causing electrolytic detachment of the coil from the wire. A similar system is used to deliver a coil to the site of an arterio-venous malformation or fistula. The subject system provides a mechanical alternative to prior art electrolytic detachment systems.

BRIEF DESCRIPTION OF THE DRAWINGS

FIG. 2 is a side elevation view of the embolic coil of the implant system of FIG. 1;

FIG. 3A-3C are a series of side elevation views of the portion of the coil identified by region 3-3 in FIG. 2, illustrating the properties of the pre-tensioned stretch resistant wire.

FIG. 4A illustrates the proximal portion of the coil engaged with the distal portion of the detachment shaft and wire.

FIG. 4B is similar to FIG. 4A and illustrates the proximal portion of the coil and the distal portion of the shaft and wire following detachment.

FIGS. 6A and 6B schematically illustrate steps of detaching the coil from the detachment shall and wire in accordance with the method of FIGS. 5A through 5G.

FIG. 7 is an elevation view of an alternate embodiment of a detachment system, in which the distal end of the pusher tube is shown partially transparent.

FIG. 8 is a perspective view of the embodiment of FIG. 7.

FIG. 9 is a plan view of the system of FIG. 7, showing the coil detached from the pusher tube.

FIG. 10 is an elevation view of the system of FIG. 7, showing the coil detached from the pusher tube.

FIG. 12 is a plan view of the embodiment of FIG. 11.

FIG. 14 is a side elevation view of the embodiment of FIG. 11 following a step in detachment of the embolic coil.

FIG. 15 is a side elevation view of the embodiment of FIG. 11 following detachment of an embolic coil.

FIG. 16 is a side elevation view of yet another alternative embodiment according to the invention.

DETAILED DESCRIPTION OF THE INVENTION

Figure 1:
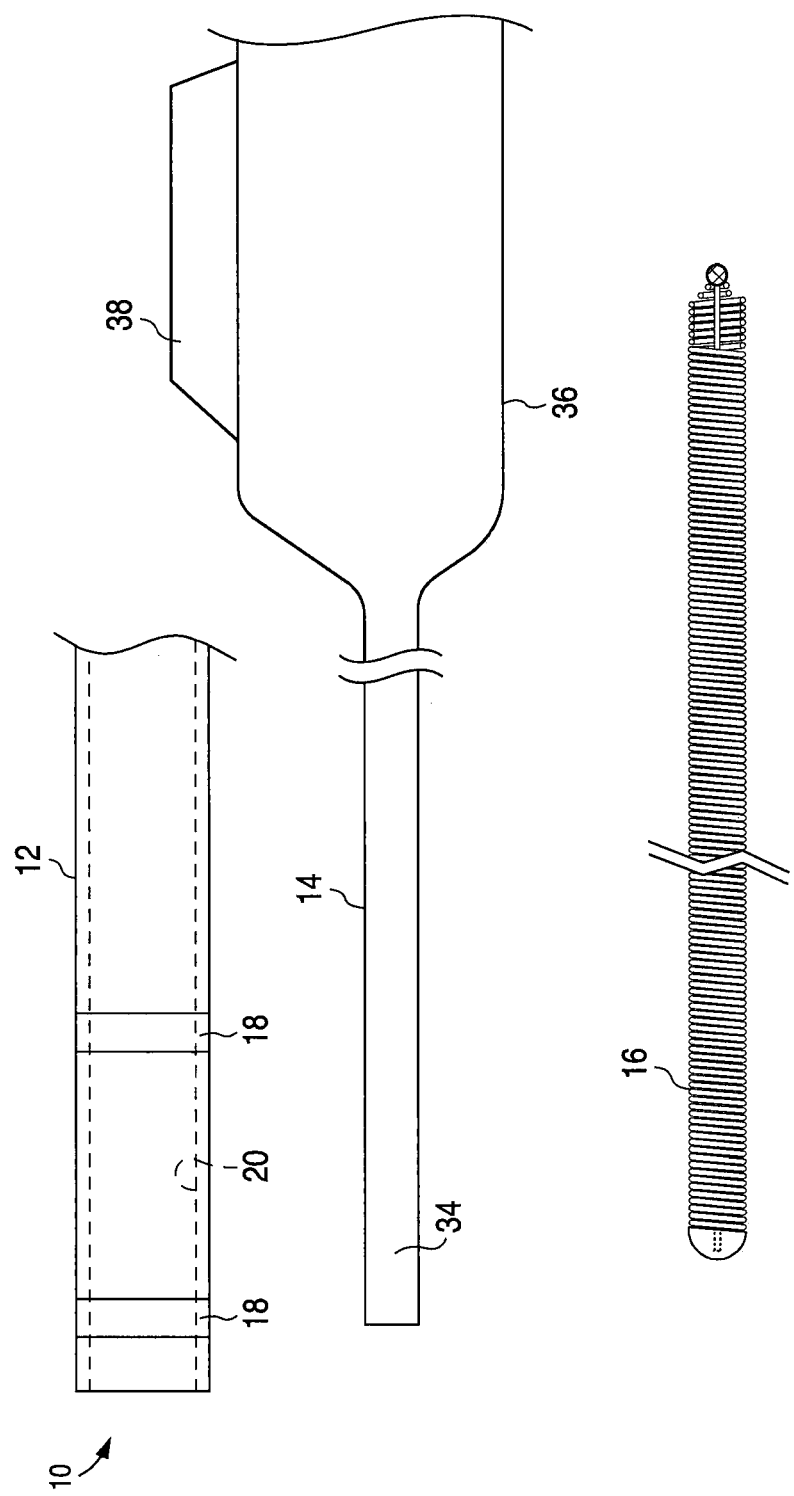
FIG. 1 is a side elevation view of an embolic coil implant system.

Referring to FIG. 1, general components of an embolic coil implant system 10 include a microcatheter 12, insertion tool 14, and embolic coil 16. These components may be provided individually or packaged together. Additional components of the system may include a guide catheter insertable into the vasculature via an access point (e.g., femoral puncture), and an associated guide wire for facilitating advancement of the guide catheter.

Microcatheter 12 is an elongate flexible catheter proportioned to be received within the lumen of a corresponding guide catheter and advanced beyond the distal end of the guide catheter to the cerebral vasculature where an aneurysm to be treated is located. Suitable dimensions for the microcatheter include inner diameters of 0.010" to 0.045", outer diameters of 0.024" to 0.056", and lengths from 75 cm to 175 cm. One preferred embodiment utilizes the following dimensions: 0.025 in ID, 0.039 in Distal OD (3 F), 0.045 in Proximal OD (3.5 F), and length of 145-155 cm. Marker bands 18 facilitate fluoroscopic visualization of the microcatheter position during the course of an implantation procedure. Microcatheter 12 includes a lumen 20 proportioned to receive the embolic coil 16 and the shaft of the insertion tool 14. When the coil is within the lumen of the microcatheter, the surrounding lumen walls restrain the coil in the generally elongated shape shown in FIG. 1. Release of the coil from the microcatheter allows the coil to assume its secondary shape.

Details of the embolic coil 16 are shown in FIG. 2. Coil 16 is formed of a wire 22 coiled to have a primary coil diameter D1 of approximately 0.020 inches, although smaller diameters, and diameters as large as 0.035 inches, may instead be used. The pitch of the coil may be uniform as shown, or it may vary along the length of the coil, or different sections of the coil may be formed to have different pitches. The wire material selected for the coil is preferably one capable of fluoroscopic visualization, such as Platinum/Iridium, Platinum/Tungsten, or other suitable material. In one embodiment, the wire forming the coil has a diameter of approximately 0.0015-0.0020 inches. Coil 16 is then formed into a secondary three-dimensional shape. The secondary shape can be helical, spherical, multi-lobal or any other shape desired to fill the aneurysm void. 'The process for forming this shape is to temperature set the stretch resistant wire 30 into the desired shape. The stretch-resistant member could be a shape-memory polymer or metal such as nitinol. Stretch-resistant member 30 can be in a diameter range of 0.0005" to 0.003".

One or more reduced-diameter windings 24 are positioned at the proximal end of the coil 16, forming a stop 26. An atraumatic distal tip 28, which may be formed of gold or tin solder or other material, is mounted to the distal end of the coil 16. A stretch resistant wire 30 or other type of elongate filament or strand is attached to the distal tip 28 and extends through the coil 16. Stretch resistant wire 30 includes an element 32 on its proximal end that is sufficiently broad that it will not pass through the lumen of the windings of stop 26, but will instead rest against the stop 26. Element 32 may be a ball (e.g., formed of gold/tin solder, PET, platinum, titanium or stainless steel) as shown, or an alternative element having features that will engage with or be unable to pass the stop 26 or other parts of the proximal portion of the coil 16. The stretch resistant wire helps to maintain the pitch of the coil even when the coil is placed under tension. During implantation, the stretch resistant wire helps in repositioning of the coil (if needed). The stretch resistant wire makes the coil easier to retract, and maintains close positioning of coil windings during manipulation of the coil.

Stretch resistant wire 30 is pre-tensioned, so that the ball 32 naturally sits firmly against the stop 26 as shown in FIG. 3A. When tension is applied to the wire 30 as shown in FIG. 3B, and then released as in FIG. 3C, the ball will return to its firm seating against the stop. The stretch resistant wire prevents the coil from stretching when deployed, repositioned, or withdrawn from the aneurysm. This stretch resistant wire will not yield when placed in tension during repositioning. Conversely, stretch resistant wire will prevent compaction of adjacent coils, likely improving long term performance of coil 16 following implantation. Stretch resistant wire 30 will have a yield strength approximately 0.5 lbs. In a preferred embodiment, the stretch resistant wire is shape set to give the embolic coil 16 its predetermined secondary shape. In other words, the shape set of the wire will cause the coil 16 to assume the secondary shape (FIG. 5C) once it is advanced from the microcatheter 12. In alternative embodiments, the coil itself, or both the coil and the wire may be shape set to give the coil its secondary shape.

Referring again to FIG. 1, insertion tool 14 includes a flexible elongate tubular shaft 34, and a handle 36 on the proximal portion of the shaft 34. An actuator 38 on the handle 36 is manipulatable by a user to effect detachment of an embolic coil from the shaft 34 as will be discussed in detail below. Although the actuator is shown in this drawing as a slidable button, any number of other types of slidable, rotatable, pivotable, depressible, etc., actuators may instead be used using techniques well known in the art. Although the handle 36 is shown coupled to insertion tool 14, in other embodiments, the handle 36 may be attached and removed for use with multiple coils to effect detachment.

FIGS. 4A and 4B show cross-section views of the distal portion of the shaft 34. As shown, a detachment wire 40 or other type of elongate filament or strand extends through the lumen of the shaft 34. During use, shaft 34 would be inserted through microcatheter 12 to the aneurysm. A pair of engaging elements 42 is positioned on the wire 40. Engaging elements 42 are elements that will couple the detachment wire 40 to the stretch resistant wire 30, preferably by engaging the element 32. In the illustrated embodiment, the engaging elements 42 are spaced apart elements having a broader diameter than the wire. Suitable examples include spaced apart beads 42 deposited onto the wire. These may be formed of gold/tin solder, PET, stainless steel, or alternate materials.

As shown in FIG. 4A, embolic coil 16 is coupled to the insertion tool 14 by positioning ball 32 between the engaging elements 42 within the shaft 34. The ball 32 is constrained between the engagement elements 42 and the surrounding walls of the shaft lumen. This positioning retracts the ball 32 proximally relative to the coil 16, adding tension to the stretch resistant wire 30.

Referring to FIG. 4B, to release the embolic coil 16 from the insertion tool 14, the actuator is manipulated to cause relative advancement of the detachment wire 40 relative to the shaft 34. In other words, the actuator may withdraw the shaft and/or advance the wire 40. Other embodiments may be provided without an actuator, in which case the user may manually advance the wire 40 and/or retract the shaft 34. The more proximal sections of the wire 40 and/or shaft 34 may be thicker than the distal sections as shown in FIGS. 6A and 6B to facilitate manual actuation by the user's fingers or by an actuator.

The relative movement between the shaft and wire causes the distal portion of the wire 40 to extend from the shaft, thereby releasing the constraints on the ball 32. The ball 32 and attached stretch resistant wire 30 retract towards the coil 16, and the ball 32 comes to rest at the stop 26.

FIGS. 5A through 5G illustrate use of the system to implant the coil 16. Prior to implantation, the coil is coupled to the insertion tool 14 as illustrated in FIG. 1.

Figure 5A:
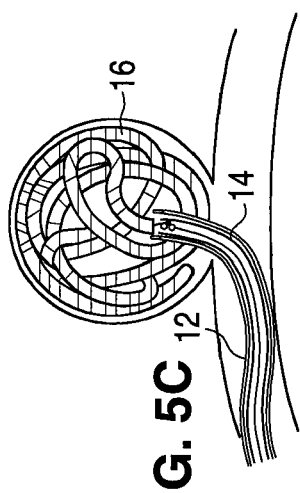
FIGS. 5A through 5G are a sequence of drawings schematically illustrating the steps of occluding an aneurysm using the system of FIGS. 1 through 4B.

The microcatheter 12 is introduced into the vasculature using a percutaneous access point, and it is advanced to the cerebral vasculature. As discussed above, a guide catheter and/or guide wire may be used to facilitate advancement of the microcatheter. The microcatheter is advanced until its distal end is positioned at the aneurysm A. FIG. 5A.

Figure 5B:
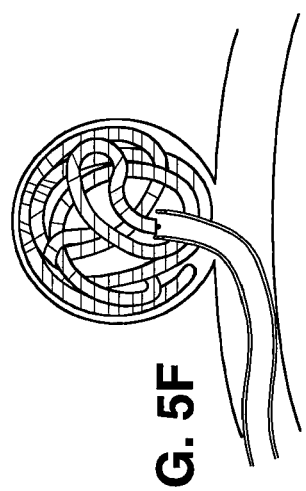
Figure 5C:
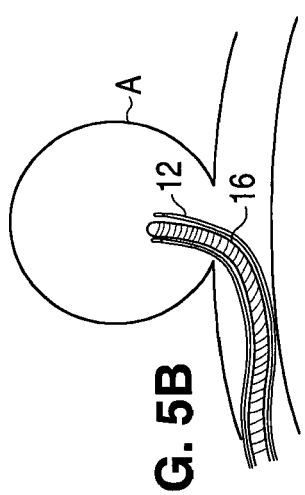

The coil 16 is advanced through the microcatheter 12 to the aneurysm A. FIG. 5B. The coil and insertion tool may be pre-positioned within the microcatheter 12 prior to introduction of the microcatheter 12 into the vasculature, or they may be passed into the proximal opening of the microcatheter lumen after the microcatheter has been positioned within the body. The insertion tool 14 is advanced within the microcatheter 12 to deploy the coil from the microcatheter into the aneurysm A. As the coil exits the microcatheter, it assumes its secondary shape as shown in FIG. 5C due to the shape set of the stretch resistant wire 30.

Referring to FIG. 6A, the detachment wire 40 may include fluoroscopically visible markers that indicate to the user when the coil has been advanced sufficiently for detachment. For example, the user may watch for alignment of a marker 44 on the wire 40 with the markers 18 on the microcatheter. Note, however, that the detachment step may be performed with the proximal end of the coil inside or outside the microcatheter.

Figure 5D:
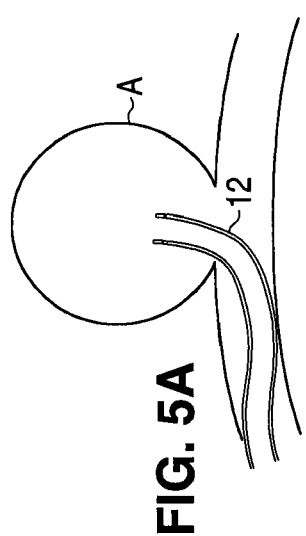
Figure 5E:
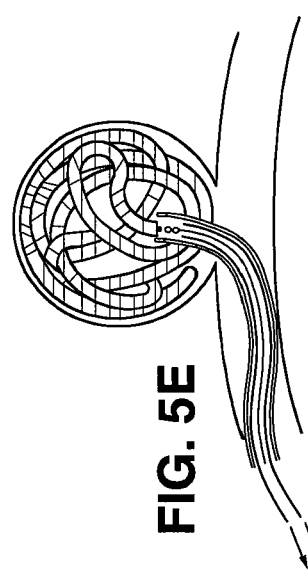
Figure 5F:
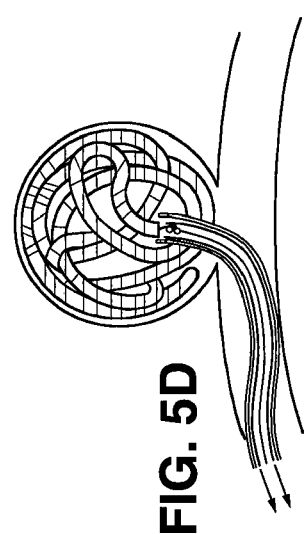
Figure 5G:
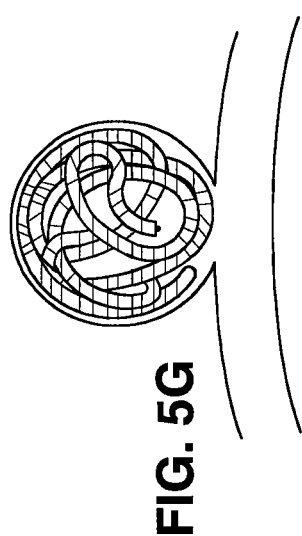

At the appropriate time, the coil is released from the insertion tool by withdrawing the shaft 34 relative to the detachment wire 30 to cause the distal end of the wire to extend from the shaft 34. FIGS. 5D and 6B illustrate retraction of the shaft 34 while holding the wire 30 stationary, although the detachment may instead be performed by advancing the wire while holding the shaft stationary, or by combined motion of retracting the shaft and advancing the wire. The coil detaches from the wire 30, and the ball 32 of the coil 16 retracts into contact with the stop 26. FIG. 5E. The insertion tool 14 is withdrawn from the microcatheter 12. FIG. 5F. If additional coils are to be implanted, an insertion tool 14 with an attached coil is passed into the microcatheter 12 and the steps of FIGS. 5B through 5E are repeated. The method is repeated for each additional coil need to sufficiently fill the aneurysm A. Once the aneurysm is fully occluded, the microcatheter 12 is removed. FIG. 5G.

FIGS. 7-10 illustrate an alternative embodiment of an insertion tool 114 that may be used to deploy the embolic coil 16 in the manner similar to that shown in FIGS. 5A-5G.

Referring to FIG. 7, the insertion tool 114 comprises an elongate pusher tube 116 having a tubular distal tip 118 (shown partially transparent in FIG. 7). A fulcrum 120 having a slot 122 (best shown in FIG. 9) is cut into a side wall of the distal tip 118. The distal end of the fulcrum can be moved into an inwardly-extending position in which it extends into the lumen of the distal tip 118 as shown in FIGS. 7 and 8. The fulcrum 120 is shape set to return to an open (or neutral) position generally flush with the pusher tube wall (FIG. 9) when it is released from the inwardly-extending position. A pull wire 126 is extendable through the lumen of the pusher tube 116 and into the slot 122 in the fulcrum 120 to retain the fulcrum in the inwardly-extending position shown in FIGS. 7 and 8.

The distal tip 118 is preferably formed of shape memory material such as nitinol, shape memory polymer, or an injection molded material having elastic properties. The more proximal sections of the pusher tube 116 can be made of polymeric tubing, with the distal tip 118 mounted to polymeric tubing. In the illustrated embodiment, the distal tip 118 includes a plurality of proximally-extending fingers 124 laminated into the polymeric tubing of the pusher tube 116 to secure the distal tip in place.

To couple the pusher tube 116 and coil 16 for use, the pull wire 126 is introduced into the pusher tube. Ball 32 is separated slightly from the coil 16 and is inserted into the pusher tube 116 and held in place while the fulcrum 120 is pressed into the inwardly-extending position to prevent movement of the ball 32 out of the distal tip 118. The pull wire 126 is passed through the slot 122 to retain the fulcrum in the inwardly-extending position.

To deploy the coil 16, the coil and pusher tube 116 are passed through a delivery catheter as described above. At the site of the aneurysm, the pusher tube 116 is advanced to push the coil out of the delivery catheter. The pull wire 126 is pulled proximally from the slot 122 of the fulcrum 120, allowing the fulcrum 120 to return to its open position and out of contact with the ball 32. As with the previous embodiments, the ball 32 retracts into contact with the proximal end of the coil 16 and in doing so exits the proximal end of the pusher tube 116.

Figure 11:
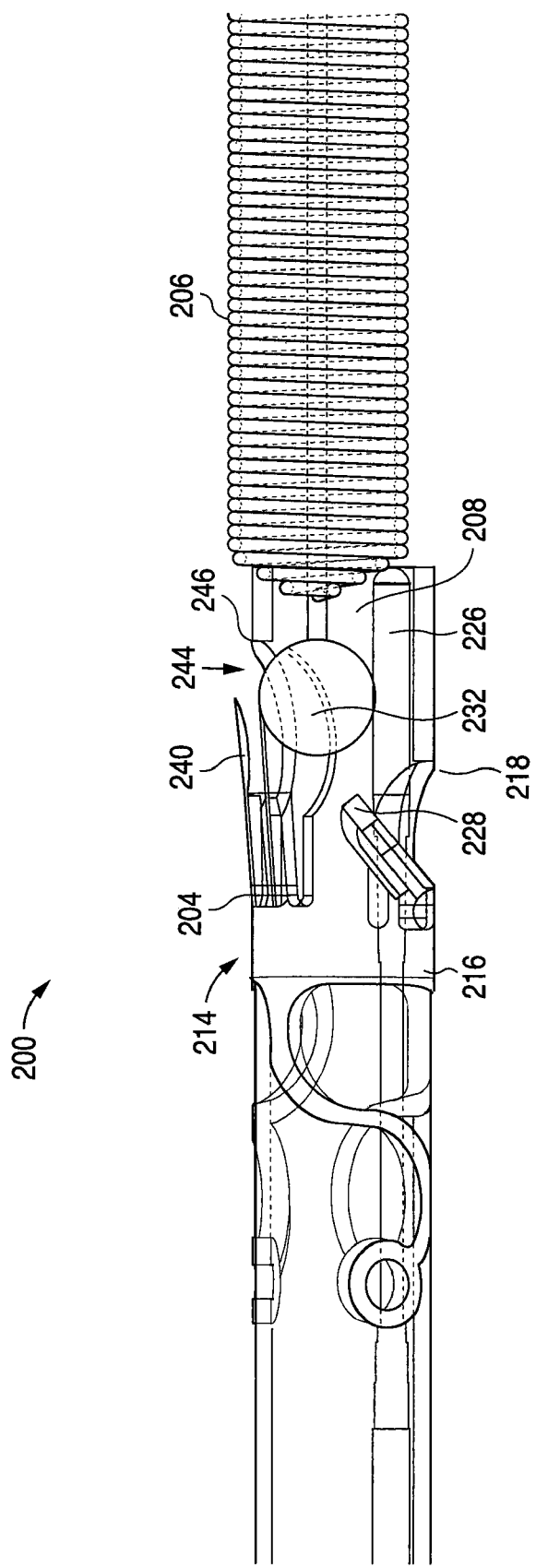
FIG. 11 is a side elevation view of yet another embodiment of a detachment system according to the invention, in which the distal end of the pusher tube is shown partially transparent.
Figure 13:
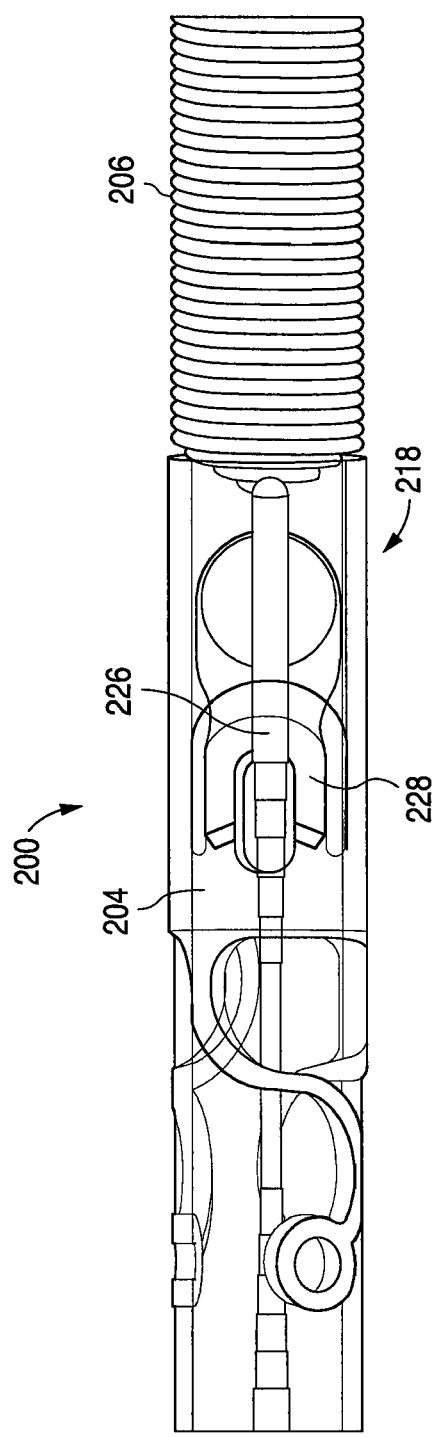
FIG. 13 is a bottom view of the embodiment of FIG. 11.

FIGS. 11-15 illustrate another alternate embodiment of a detachment system. FIGS. 11, 14 and 15 illustrate detachment system 200 following successive steps to detach embolic coil 206 from insertion tool 214. Beginning with FIG. 11, a side elevation view of the distal end of insertion tool 214 is shown as partially transparent. Insertion tool 214 comprises an elongate pusher tube 216 having a tubular distal tip 218, and side wall 204 defining lumen 208 therethrough. Side wall 204 is cut, molded, or otherwise configured to define paddle 240, partial aperture 244 surrounding a portion of paddle 240, and shoulder 246. Paddle 240 and partial aperture 244 may be of various alternative sizes and/or shapes. An example of a suitable shape for paddle 240 can be seen in a plan view in FIG. 12, which also reveals a possible position of ball 232 prior to deployment of system 200. As explained in greater detail below, prior to deployment of system 200 to release coil 206, ball 232 has freedom of movement within lumen 208, both axially and rotationally. The exact position of ball 232 will consequently vary from that illustrated in FIG. 12.

Also cut or otherwise configured or disposed upon a side wall 204 is alignment member 228, shown in the example of FIG. 11 as opposite paddle 240. As seen from a bottom view of the device in FIG. 13, alignment member is illustrated as a loop cut from sidewall 204. Alternatively, an alignment member may be formed by placing one or more circumferential cuts into the sidewall to define a band and bending the band inwardly into the lumen. It will be appreciated that alignment member 228 may alternatively be, for example, a hook, tab, or any other suitable structure for guiding the position of pull wire 226. Pull wire 226 is axially moveable within alignment member 228, however, alignment member 228 helps prevent unintended longitudinal translation of pull wire 226.

In preparation for deploying system 200, pull wire 226 is loaded through alignment member 228, through lumen 208, until it reaches ball 232, or as far as coil 206. Prior to loading coil 206, pull wire 226, which may be tapered, may be threaded through the distal end of insertion tool 214 to permit loading of ball 232, and then retracted slightly to releasably retain coil 206. When positioned within distal tip 218 via alignment member 228, and occupying lumen 208 pull wire 226 urges ball 232 against paddle 240, and ball has freedom of movement within aperture 244. Partial aperture 244 permits paddle 240 to be urged slightly out of the plane of sidewall 204, and paddle 240 in turn places some pressure on ball 232. Ball 232 is prevented by shoulder 246 from exiting the distal tip 218. Though ball 232 is retained within distal tip of insertion tool 214 prior to deployment of system 200, ball 232 advantageously has both axial and rotational freedom of movement within the distal tip 218 of insertion tool 214 prior to retraction of pull wire 226 by an operator.

As shown in FIG. 14, during deployment of detachment system 200, pull wire 226 is retracted proximally of ball 232. (Alternatively, insertion tool 214 may be moved distally to pull wire 226.) Once pull wire 226 is proximal of ball 232, ball 232 is urged by paddle 240 into the lumen 208 of insertion tool 214. Axial movement of ball 232 is no longer restricted in a distal direction by shoulder 246, and ball 232 (and hence coil 206) is free to exit distal tip 218. FIG. 15 illustrates coil 206 following its exit from distal tip 218.

FIG. 16 illustrates a similar detachment mechanism which operates generally according to the same principles of the embodiment described in relation to FIGS. 11-15 above. However, in the embodiment illustrated in FIG. 16, paddle 340 is oriented perpendicularly to the longitudinal access of insertion tool 214. Further, no aperture surrounds paddle 340. Other, alternative configurations of paddle 340 are also possible according to the invention.

What is claimed is:

1. An embolic coil deployment system for releasing an embolic coil, comprising:
    an elongated shaft having a proximal end and a distal end, and a lumen configured to receive and releasably retain an embolic coil therein, the elongated shaft further comprising a sidewall;
    a filament that is axially translatable within the lumen of the elongated shaft; and
    a paddle disposed on the sidewall, wherein the paddle selectively retains the embolic coil within the lumen in a first orientation and releases the embolic coil in a second orientation,
    wherein the filament has a first position for retaining the embolic coil and a second position for releasing the embolic coil, and
    wherein the filament is positioned distally in the first position and is positioned proximally in the second position.

2. The embolic coil deployment system of claim 1, wherein the paddle has a proximal end attached to the sidewall and a free distal end.

3. The embolic coil deployment system of claim 2, including an aperture formed in the sidewall of the elongated shaft.

4. The embolic coil deployment system of claim 3, wherein the paddle is at least partially disposed within the aperture.

5. The embolic coil deployment system of claim 3, wherein the aperture at least partially surrounds the free distal end of the paddle.

6. The embolic coil deployment system of claim 3, wherein the embolic coil is at least partially disposed within the aperture when the paddle selectively retains the embolic coil.

7. The embolic coil deployment system of claim 3, wherein a distal edge of the aperture defines a shoulder that selectively retains the embolic coil when the paddle is in the first orientation.

8. The embolic coil deployment system of claim 1, including an alignment member for orientating the filament opposite of the paddle.

9. The embolic coil deployment system of claim 1, wherein the first position of the filament secures the embolic coil against the paddle and the second position releases the embolic coil from the paddle.

10. The embolic coil deployment system of claim 1, wherein the paddle in the first orientation bends outwards from the lumen of the elongated shaft.

11. The embolic coil deployment system of claim 1, wherein the paddle in the second orientation bends inwards towards the lumen of elongated shaft.

12. The embolic coil deployment system of claim 1, wherein the paddle is biased towards the second orientation.

13. The embolic coil deployment system of claim 1, wherein the sidewall lies in a curved plane, said paddle is flexible out of the curved plane and is biased into the lumen of the elongated shaft.

14. The embolic coil deployment system of claim 1, wherein the paddle is biased towards the second orientation, whereby the embolic coil in the lumen of the elongated shaft and the filament in the first position press the paddle towards the first orientation.

15. The embolic coil deployment system of claim 1, wherein the embolic coil includes a retention element configured to engage the paddle.

* * * * *